(12) United States Patent
Gormley et al.

(10) Patent No.: US 6,432,971 B2
(45) Date of Patent: *Aug. 13, 2002

(54) METHOD OF PREVENTION OF PROSTATIC CARCINOMA WITH 17β-N-MONOSUBSTITUTED-CARBAMOYL-4-AZA-5α-ANDROST-1-EN-3-ONES

(75) Inventors: Glenn J. Gormley; Elizabeth Stoner, both of Westfield, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/875,381

(22) Filed: Jun. 6, 2001

Related U.S. Application Data

(62) Division of application No. 08/364,072, filed on Dec. 27, 1994, now Pat. No. 6,268,376, which is a continuation of application No. 08/190,769, filed on Feb. 2, 1994, now abandoned, which is a continuation of application No. 08/016,474, filed on Feb. 10, 1993, now abandoned, which is a continuation of application No. 07/808,510, filed on Dec. 17, 1991, now abandoned.

(51) Int. Cl.$^7$ .............................................. A61K 31/44

(52) U.S. Cl. .................................................... 514/284

(58) Field of Search ......................................... 514/284

(56) References Cited

U.S. PATENT DOCUMENTS

| 4,760,071 A | 7/1988 | Rasmusson et al. |
| 4,845,104 A | 7/1989 | Carlin et al. |
| 5,300,294 A | 4/1994 | Johnson |
| 5,302,621 A | 4/1994 | Kojima et al. |

FOREIGN PATENT DOCUMENTS

| EP | 0 004 949 A1 | 10/1979 |
| EP | 0 200 859 | 11/1986 |
| EP | 0 277 002 | 8/1988 |
| EP | 0 285 383 | 10/1988 |
| EP | 0 414 491 A2 | 2/1991 |
| EP | 0 428 366 A2 | 5/1991 |
| EP | 0 462 662 | 12/1991 |
| EP | 0 271 220 B1 | 1/1992 |
| EP | 0 547 687 A1 | 6/1993 |
| EP | 0 547 691 A1 | 6/1993 |
| WO | WO 91/12261 | 8/1991 |
| WO | WO 92/00010 | 1/1992 |

OTHER PUBLICATIONS

Brawer et al., Cancer 75(7), pp. 1783–1789 (1995), "Chemoprevention for prostate cancer".

Presti, Jr., et al., J. Urology, vol. 148 (1992), pp. 1201–1204, "Multicenter, randomized, double–blind, placebo controlled study to investigate the effect of finasteride (MK–906) on Stage D prostate cancer".

Gormley et al., "A placebo controlled study of finasteride (MK–906) on Stage D prostate cancer", abstract of talk given at the American Urol. Assoc. Mtg. in Jun. 1991 in Toronto, Canada.

Gormley et al., Urologic Clinics of No. America, vol. 18, pp. 93–98 (1991), "Role of 5α–reductase inhibitors in the treatment of advanced prostatic carcnoma".

Gormley et al., "Effect of finasteride on serum PSA levels in men with prostate cancer", at the Prostate Cancer 2nd Int'l Update in Denver, CO (Jan. 18, 1992).

Huggins et al., Cancer Research, pp. 293–297 (1941), "Studies on Prostatic Cancer: I. Effect of castration, of estrogen and androgen injection on serum phosphatases in metastatic carcinoma of the prostate".

Metcalf et al., TIPS, vol. 10, pp. 491–495 (1989), "Inhibitors of steroid 5α–reductase in benign prostatic hyperplasia, male pattern baldness and acne".

Kadohama et al., JNCI, vol. 71, No. 2, pp. 475–481 (1985), "Retardation of prostate tumor progression in the nobel rat by 4–methyl–4–aza–steroidal inhibitors of 5α–reductase".

Rainwater et al., Mayo Clinic Proc., vol. 65, pp. 1118–1126 (1990), "Prostate–specific antigen testing in untreated and treated prostatic adenocarcinoma".

Arai et al., J. of Urology, vol. 144, pp. 1415–1419 (1990), "Prognostic significance of prostate specific antigen in endocrine treatment for prostatic cancer".

Hudson et al., J. of Urology, vol. 142, pp. 1011–1017 (1989), "Clinical use of prostate specific antigen in patients with prostate cancer".

(List continued on next page.)

*Primary Examiner*—Jerome D. Goldberg
(74) *Attorney, Agent, or Firm*—Catherine D. Fitch; Melvin Winokur

(57) ABSTRACT

17β-N-monosubstituted-carbamoyl-4-aza-5α-androst-1-en-3-ones of the formula

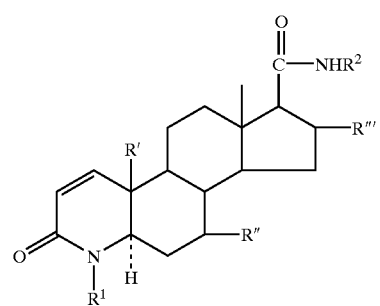

wherein $R^1$ is selected from hydrogen, methyl and ethyl and $R^2$ is a straight or branched chain alkyl, cycloalkyl, aralkyl of from 1–12 carbons, or monocyclic aryl optionally containing 1 or more lower alkyl substituents of 1–2 carbon atoms and/or 1 or more halogens, and R', R", R''' are hydrogen or methyl are useful for the prevention of prostatic carcinoma.

8 Claims, No Drawings

OTHER PUBLICATIONS

Brawer et al., Supp. to Urology, vol. 33, No. 5, pp. 11–16 (1989), "Prostate–specific antigen in management of prostatic carcinoma".

Stamey et al., N. Eng. J. of Medicine, vol. 317, pp. 909–916 (1987), "Prostate–specific antigen as a serum marker for adenocarcinoma of the prostate".

Walsh et al., Therapeutic Progress in Urological Cancers, pp. 27–33 (1989), "The value of prostate–specific antigen in the management of localized prostatic cancer".

Stamey et al., J. of Urology, vol. 141, pp. 1070–1075 (1989), "Prostate specific antigen in the diagnosis and treatment of adenocarcinoma of the prostate".

Lange et al., J. of Urology, vol. 141, pp. 873–879 (1989), "The value of serum prostate specific angiten determinations before and after radical prostatectomy".

Hoehn et al., The Prostate, vol. 1, pp. 95–104 (1980), "Human prostatic adenocarcinoma: Some characteristics of a serially transplantable line in nude mice (PC 82)".

Brooks et al., The Prostate, 18:215–227 (1991), "Effect of castration, DES, flutamide, and the 5α–reductase inhibitor, MK–906, on the growth of the dunning rat prostatic carcinoma, R–3327".

J. of Andrology, vol. 12(6), pp. 372–375 (1991), "The MK–906 (Finasteride) Study Group: One year experience in the treatment of benign prostatic hyperplasia with finasteride".

Bologna et al., Current Therap. Res., vol. 51 (1992), "Anti-androgens and 5–alpha reductase inhibition of the proliferation rate in PC3 and DU145 hunan prostatic cancer cell lines" no copy.

Lamb et al., The Prostate, vol. 21 (1992), pp. 15–34, "Response of rat and human prostatic cancers to the novel 5α–reductase inhibitor, SK & F 105657" no copy.

Rasmusson et al., J. Med. Chem., vol. 29 (1986), pp. 2298–2315, "Azasteroids: Structure–activity relationships for inhibition of 5α–reductase and of androgen receptor binding" no copy.

Tsukamoto et al., J. of the Nat'l Cancer Institute, vol. 87 (1995), pp. 842–843, "Chemoprevention of rat prostate carcinogenesis by use of fiansteride or casodex" no copy.

Andriole et al., Urology, vol. 45 (1995), pp. 491–497, "Treatment with finasteride following radical prostatectomy for prostate cancer" no copy.

Gormley et al., "Hormonal effects of finasteride in men with prostatic cancer after radical prostatectomy", an abstract for presentation at Endocrine 1994 Society Meeting, Los Angeles, CA Jun. 1994 no copy.

Carter et al., "Chemotherapy of Cancer", 2nd ed., John Wiley & Sons, New York, NY (1981), pp. 3–10.

Stedman, "Stedman's Medical Dictionary", 24th ed. (1982), pp. 675–677.

METHOD OF PREVENTION OF PROSTATIC CARCINOMA WITH 17β-N-MONOSUBSTITUTED-CARBAMOYL-4-AZA-5α-ANDROST-1-EN-3-ONES

CROSS REFERENCE TO RELATED APPLICATIONS

The present application is a divisional application of granted U.S. application Ser. No. 08/364,072, filed Dec. 27, 1999 now U.S. Pat. No. 6,265,376; which is a continuation of application Ser. No. 08/190,769, filed Feb. 2, 1994, presently abandoned; which is a continuation of application Ser. No. 08/016,474, filed Feb. 10, 1993, presently abandoned; which, in turn, is a continuation of application Ser. No. 07/808,510, filed Dec. 17, 1991, presently abandoned.

BACKGROUND OF THE INVENTION

The present invention is concerned with the use of 17β-N-monosubstituted-carbamoyl-4-aza-5α-androst-1-en-3-one compounds as testosterone-5α-reductase inhibitors for the prevention of prostatic carcinoma.

DESCRIPTION OF THE PRIOR ART

There is no drug which is known to prevent prostatic cancer to date. Most forms of androgen withdrawal result in sexual dysfunction and gynecomotia making them unacceptable for prevention therapy.

It is further well known in the art that certain undesirable physiological manifestations, such as acne vulgaris, seborrhea, female hirsutism, male pattern baldness and benign prostatic hypertrophy, are the result of hyperandrogenic stimulation caused by an excessive accumulation of testosterone or similar androgenic hormones in the metabolic system. It is also established that androgens play an important role in prostatic carcinoma. Boys castrated prior to puberty or with a metabolic deficiency of androgens do not develop prostatic cancer. Early attempts to provide a chemotherapeutic agent to counter the undesirable results of hyperandrogenicity resulted in the discovery of several steroidal antiandrogens having undesirable hormonal activities of their own. The estrogens, for example, not only counteract the effect of the androgens but have a feminizing effect as well. Non-steroidal anti-androgens have also been developed, for example, 4'-nitro-3'-trifluoromethyl-isobutyranilide. See Neri et al., Endo., Vol. 91, No. 2 (1972). However, these products, though devoid of hormonal effects, are peripherally active, competing with the natural androgens for receptor sites, and hence have a tendency to feminize a male host or the male fetus of a female host.

It more recently became known in the art that the principal mediator of androgenic activity in some target organs is 5α-dihydrotestosterone, and that it is formed locally in the target organ by the action of testosterone-5α-reductase. It therefore has been postulated and demonstrated that inhibitors of testosterone-5α-reductase will serve to prevent or lessen symptoms of hyperandrogenic stimulation. Nayfe et al., Steroids, 14, 269 (1969) demonstrated in vitro that methyl 4-androsten-3-one-17β-carboxylate was a testosterone-5α-reductase inhibitor. Then Voigt and Hsia, Endocrinology, 92, 1216 (1973), Canadian Pat. No. 970,692, demonstrated that the above ester and the parent free acid, 4-androsten-3-one-17β-carboxylic acid are both active inhibitors of testosterone-5α-reductase in vitro. They further demonstrated that topical application of either testosterone or 5α-dihydrotestosterone caused enlargement of the female hamster flank organ, an androgen dependent sebaceous structure. However, concomitant administration of 4-androsten-3-one-17β-carboxylic acid or its methyl ester inhibited the response elicited by testosterone but did not inhibit the response elicited by 5α-dihydrotestosterone. These results were interpreted as indicating that the compounds were antiandrogenic by virtue of their ability to inhibit testosterone-5α-reductase.

A number of 4-aza steroid compounds are known. See, for example, U.S. Pat. Nos. 2,227,876; 3,239,417; 3,264,301; and 3,285,918; French Pat. No. 1,465,544; Doorenbos and Solomons, J. Pharm. Sci. 62, 4, pp. 638–640 (1973); Doorenbos and Brown, J. Pharm. Sci., 60, No. 8, pp. 1234–1235 (1971); and Doorenbos and Kim, J. Pharm. Sci. 63, 4, pp. 620–622 (1974).

In addition, U.S. Pat. Nos. 4,377,584, 4,220,775, 4,760,071, 4,859,681 and 5,049,562 of Rasmusson et al. describe a group of 4-aza-17β-substituted-5α-androstan-3-ones which are said to be useful in the treatment of hyperandrogenic conditions. However, none of the cited references suggest that any of the novel 17βN-(monosubstituted) carbamoyl-4-aza-5α-androst-1-en-3-ones of the present invention would have utility in preventing prostatic cancer.

DESCRIPTION OF THE INVENTION

The present invention is concerned with preventing prostatic cancer in humans, who are asymptomatic for the disease by treating the patients with 17β-N-(monosubstituted)-carbamoyl-4-aza-5α-androst-1-en-3-one compounds. By the term "asymptomatic" as used herein, is meant that overt signs of the disease are not present, or indicated, e.g., lumps or cysts on the prostate wall. However, the patient may or may not have elevated levels of prostate specific antigen (PSA) at the start of therapy, due to the concomitant condition of benign prostatic hyerplasia.

There is no other known way to achieve this with acceptable side effects. The compounds described herein, and specifically finasteride, i.e., 17β-(N-tert-butylcarbamoyl)-4-aza-5α-androst-1-en-3-one, will lower DHT to castrate levels without lowering testosterone levels and will, therefore, not produce undesirable sexually related side effects. A daily dosage of 1–10 mg p.o. (oral) per person of finasteride will prevent men from developing prostatic cancer.

The present invention is concerned with compounds of the formula:

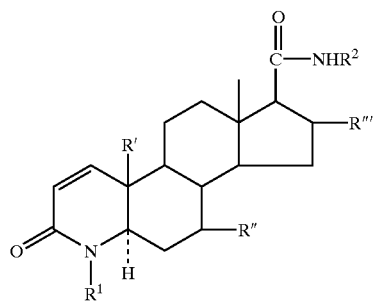

I wherein
  $R^1$ is hydrogen, methyl or ethyl.
  $R^2$ is a hydrocarbon radical selected from straight or branched chain alkyl, cycloalkyl, or aralkyl of from 1–12 carbons or monocyclic aryl optionally containing 1 or more lower alkyl substituents of from 1–2 carbon atoms and/or 1 or more halogen (Cl, F or Br) substituents.

R' is hydrogen or methyl.

R" is hydrogen or B-methyl.

R'" is hydrogen, αa-methyl or β-methyl.

A preferred embodiment of the compounds applicable in the process of our invention is represented by the formula:

II wherein

R$^1$ is hydrogen, methyl or ethyl, and

R$^3$ is branched chain alkyl, cycloalkyl, or aralkyl of from 4–10 carbons.

Representative compounds of the present invention include the following:

17β-(N-tert-amylcarbamoyl-4-aza-5α-androst-1-en-3-one,

17β-(N-tert-hexylcarbamoyl)-4-aza-5α-androst-1-en-3-one,

17β-(N-tert-butylcarbamoyl)-4-aza-5α-androst-1-en-3-one,

17β-(N-isobutylcarbamoyl)-4-aza-5α-androst-1-en-3-one,

17β-(N-tert-octylcarbamoyl)-4-aza-5α-androst-1-en-3-one,

17β-(N-octylcarbamoyl)-4-aza-5α-androst-1-en-3-one,

17β-(N-1,1-diethylbutylcarbamoyl)-4-aza-5α-androst-1-en-3-one,

17β-(N-neopentylcarbamoyl)-4-aza-5α-androst-1-en-3-one,

17β-(N-2-adamantylcarbamoyl)-4-aza-5α-androst-1-en-3-one,

17β-(N-1-adamantylcarbamoyl)-4-aza-5α-androst-1-en-3-one,

17β-(N-2-norbornylcarbamoyl)-4-aza-5α-androst-1-en-3-one,

17β-(N-1-norbornylcarbamoyl)-4-aza-5α-androst-1-en-3-one,

17β-(N-phenylcarbamoyl)-4-aza-4-methyl-5α-androst-1-en-3-one,

17β-(N-benzylcarbamoyl)-4-aza-4-methyl-5α-androst-1-en-3-one,

17β-(N-tert-amylcarbamoyl-4-aza-4-methyl-5α-androst-1-en-3-one,

17β-(N-tert-hexylcarbamoyl)-4-aza-4-methyl-5α-androst-1-en-3-one,

17β-(N-tert-butylcarbamoyl)-4-aza-4-methyl-5α-androst-1-en-3-one,

17β-(N-isobutylcarbamoyl)-4-aza-4-methyl-5α-androst-1-en-3-one,

17β-(N-tert-octylcarbamoyl)-4-aza-4-methyl-5α-androst-1-en-3-one,

17β-(N-octylcarbamoyl)-4-aza-4-methyl-5α-androst-1-en-3-one,

17β-(N-1,1-diethylbutylcarbamoyl)-4-aza-4-methyl-5α-androst-1-en-3-one,

17β-(N-neopentylcarbamoyl)-4-aza-4-methyl-5α-androst-1-en-3-one, and the corresponding compounds wherein the 4-hydrogen substituent is replaced in each of the above named compounds by a hydrogen or an ethyl radical and vice versa.

Also included as representative compounds are any of the above indicated compounds having the N-branched chain alkyl substituent replaced by a methyl, ethyl, propyl, i-propyl, butyl, phenyl, benzyl, 2-, 3- or 4-tolyl, xylyl, 2-bromo or 2-chlorophenyl, 2-6-dichloro, or a 2,6-dibromophenyl substituent.

The compounds of formula I of the present invention are prepared by a method starting with the known steroid ester of the formula:

II

17β-(carbomethoxy)-4-aza-5α-androstan-3-one which includes the stages of: (1) dehydrogenating said starting material to produce the corresponding compound containing a double-bond in the 1,2-position of the A-ring; (2) converting the 17-carbomethoxy substituent into an N-monosubstituted carbamoyl substituent and, if desired; and (3) alkylating the A-ring nitrogen to introduce a N-methyl or 4-ethyl substituent into the A ring. In carrying out the process of the present invention, it is essential that Stage 1 dehydrogenation of the 1,2-position of the steroid A ring be carried out using a 4-aza-5α-androstane-3-one-compound having no substituent other than hydrogen attached to the A-ring nitrogen. Stage 2 may consist of one or more chemical steps, and if desired may take place before stage (1) or following stage (1) or stage (3).

In accordance with the process of the present invention, the products of our invention are formed by (1) heating a 17β-alkoxycarbonyl-4-aza-5α-androstan-3-one compound III with a dehydrogenating agent such as benzeneselenic anhydride in refluxing chlorobenzene to form a 17β-alkoxycarbonyl-4-aza-5α-androst-1-ene-3-one IV; (2) the formed 5α-androst-1-en-3-one compound from Step 1 is reacted with sodium hydride under anhydrous conditions in a neutral solvent such as dimethylformamide; (3) contacting the resulting reaction mixture with an alkyl (methyl or ethyl) iodide to form the corresponding 17-β-alkoxy-carbamoyl-4-alkyl-4-aza-5α-androst-1-en-3-one V; (4) subsequently hydrolyzing said 17β-alkoxycarbonyl-4-alkyl-4-aza-5α-androst-1-en-3-one with a strong base such as aqueous methanolic potassium hydroxide at the reflux temperature, followed by acidification and isolation of the resulting steroidal acid, 17β-carboxy 4-alkyl-4-aza-5α-androst-1-en-3-one VI: (5) said steroidal acid is then converted to its corresponding 2-pyridylthio ester by refluxing with triphenyl phosphine and 2,2'-dipyridyl disulfide in an inert solvent such as toluene and the resulting product 17β-(2- pyridylthiocarbonyl)-4-alkyl-4-aza-5α-androst-1-en-3-one VII is isolated by chromatography on silica gel: (6) said pyridylthio ester is then reacted with an appropriate primary amine, e.g. t-butylamine, n-butylamine, aniline, bencylamine, t-octylamine, amine in tetrahydrofuran to form the desired products 17β-N-substituted carbamoyl-4-alkyl-4-aza-5α-androst-1-en-3-one VIII which is isolated by chromatography on silica gel.

In accordance with the process of our invention the corresponding 17β(N-R$^2$-carbamoyl)-4-aza-5α-androst-1-en-3-one XIV is readily prepared from the 17β (alkoxycarbonyl)-4-aza-5α-androstone-3-one IV by repeating the above series of reaction steps but omitting Step 2 herein above, i.e. treatment of the 4-aza-5-α-androst-1-en-3-one with sodium amide followed by methyl or ethyl iodide via intermediates XII and XIII.

In accordance with a further alternate process of preparing the compounds of our invention having only hydrogen as the sole substituent on the ring A—nitrogen, the double bond in the A ring is introduced as the last step of the process. Thus, a 17β-alkoxycarbonyl 4-aza-5α-androstan-3-one III is hydrolyzed to the corresponding steroidal acid IX 17β-carboxy-4-aza-5α-androstan-3-one which in turn is converted to the corresponding pyridylthio ester, 17β(2-pyridylthiocarbonyl)-4-aza-5α-androstan-3-one, X followed by treatment of the ester with an amine of formula R$^2$—NH$_2$ wherein R$^2$ is as defined hereinabove to form a 17β(N-R$^2$-carbamoyl)-4-aza- 5α-androstone-3-one XI which is dehydrogenated as previously described to produce compound XIV, 17β-(N-R$^2$-carbamoyl)-4-aza-androst-1-en-3-one.

In another alternate method of introducing the 17β-(N-R$^2$-carbamoyl)substituent into a 17β-carboxy, androstane compound of formula VI, XII or IX, each is treated in a manner similar to the procedure described in Steroids, Vol. 35 #3, March 1980, p. 1–7 with dicyclohexylcarbodiimide and 1-hydroxybenzotriazole to form the 17β-(1-benzotriazoloxycarbonyl)-4-aza-5α-androst-1-en-3-one, VII, XIII or X, wherein X is 1-benzotriazoloxy or 17β-(1-benzotriazoloxycarbonyl)-4-aza-5α-androstan-3-one, X.

The above reactions are schematically represented in the following structural formula outline.

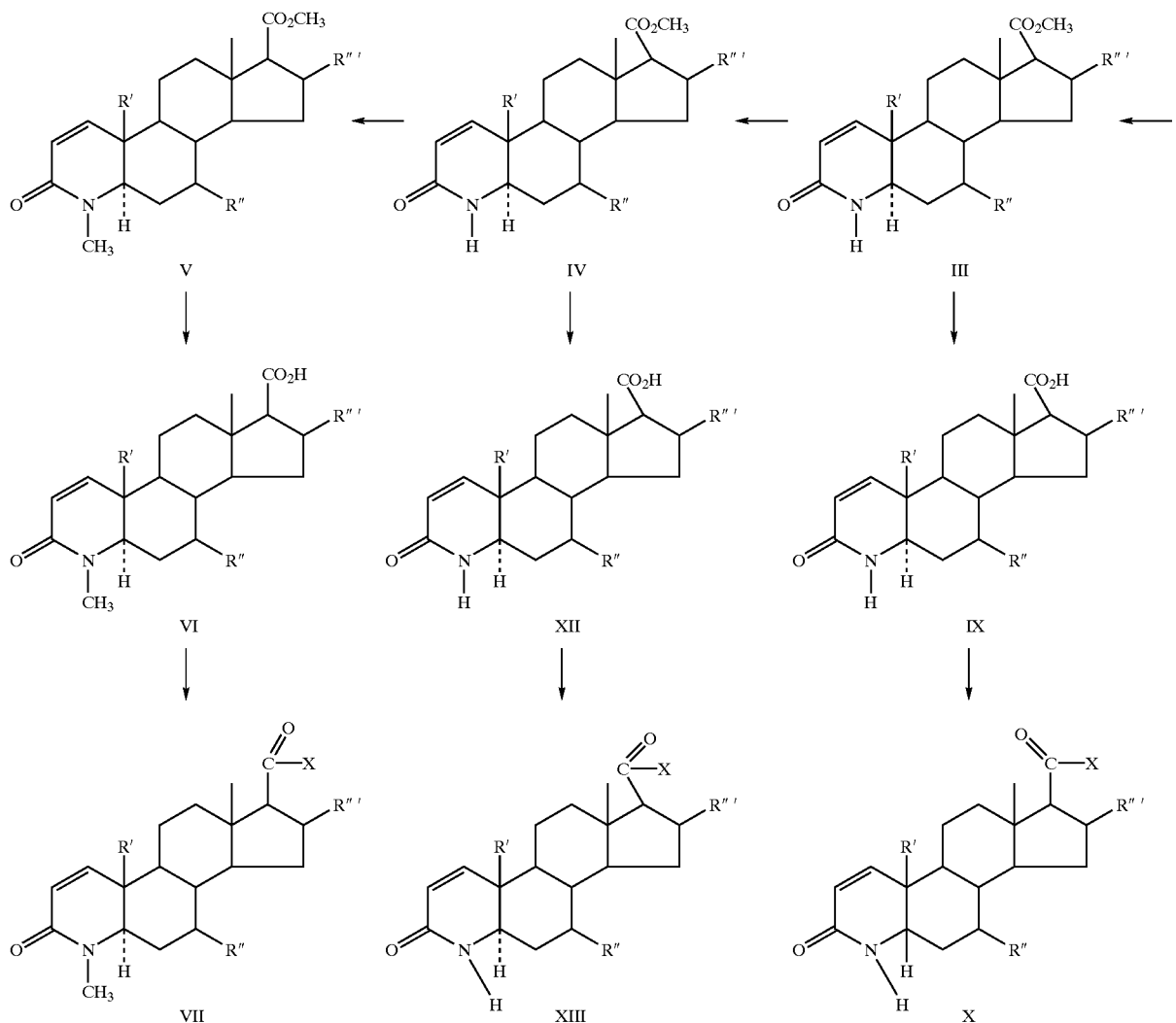

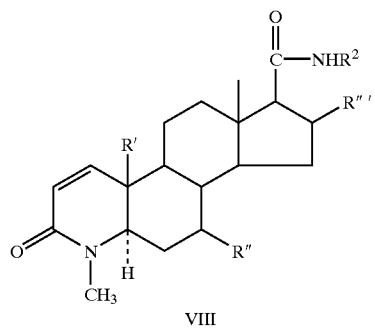

VIII

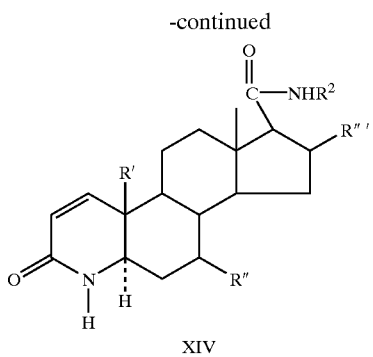

XIV

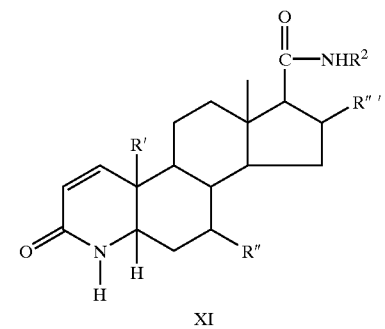

XI

X is 2-pyridylthio or benzotriazoloxy

The compounds of the present invention, prepared in accordance with the method described above, are, as already described, potent and selective antiandrogens in the prevention of prostatic cancer, by virtue of their ability to specifically inhibit testosterone-5α-reductase.

Accordingly, the present invention is particularly concerned with providing a method of treating prostatic carcinoma in human males by systemic or oral administration of the novel compounds of the present invention.

The present invention is thus also concerned with providing suitable topical and systemic pharmaceutical formulations for use in the novel methods of treatment of the present invention.

The compositions containing the compounds of the present invention as the active ingredient for use in the prevention of prostatic carcinoma can be administered in a wide variety of therapeutic dosage forms in conventional vehicles for systemic administration, as, for example, by oral administration in the form of tablets, capsules, solutions, or suspensions, of by intravenous injection. The daily dosage of the products may be varied over a wide range varying from 1 to 2,000 mg per person, preferably from 1 to 200 mg. and particularly preferred from 1 to 20 mg per person. The compositions are preferably provided in the form of scored tablets containing 0.1, 1, 5, 10, 25, 50, 100, 150, 250, and 500 milligrams of the active ingredient for the symptomatic adjustment of the dosage to the patient to be treated. An effective amount of the drug is ordinarily supplied at a dosage level of from about 0.01 mg. to about 50 mg./kg. of body weight per day. Preferably the range is from about 0.1 mg. to 7 mg./kgs. of body weight per day and more preferably from about 0.1 mg to about 3 mg/kg of body weight per day. These dosages are well below the toxic dose of the product. Capsules containing the product of this invention can be prepared by mixing an active compound of the present invention with lactose and magnesium stearate, calcium stearate, starch, talc, or other carriers, and placing the mixture in gelatin capsule. Tablets may be prepared by mixing the active ingredient with conventional tableting ingredients such as calciuim phosphate, lactose, corn starch or magnesium stearate. The liquid forms in suitably flavored suspending or dispersing agents such as the synthetic and natural gums, for example, tragacanth, acacia, methylcellulose and the like. Other dispersing agents which may be employed include glycerin and the like. For parenteral administration, sterile suspensions and solutions are desired. Isotonic preparations which generally contain suitable preservative are employed when intravenous administration is desired.

The method of preparing the novel compounds of the present invention, already described above in general terms, may be further illustrated by the following examples.

EXAMPLE 1

Methyl 3-oxo-4-aza-5α-androst-1-ene-17β-carboxylate

A suspension of 83.7 g of methyl 3-oxo-4-aza-5α-androstane-17-carboxylate* and 126.5 g of benzeneseleninic anhydride in 2.09 l of chlorobenzene was heated at reflux for 2 hours. The reflux condenser was switched to a distillation head and the mixture was distilled slowly to remove water that had formed in the reaction (2 hours). The solution was evaporated to leave 198 g of wet residue. The residue as a solution in dichloromethane was washed with saturated aqueous NaHCO₃ solution and saturated NaCl solution, then dried and evaporated to leave 172.4 g. This material was chromatographed on 2.56 kg of silica gel eluting first with dichloromethane (5 l) and then with 4:1 dichloromethane acetone. The desired product eluted after 8 l and amounted to 53.4 g. It was rinsed with diethyl ether and dried to leave 49.5 g, of the title compound m.p. 278–280° C. In a similar fashion the following compounds were converted to their corresponding 1,2-unsaturated derivatives:

* Rasmusson Johnston and Arth. U.S. Pat. No. 4,377,584, March 22, 1983.

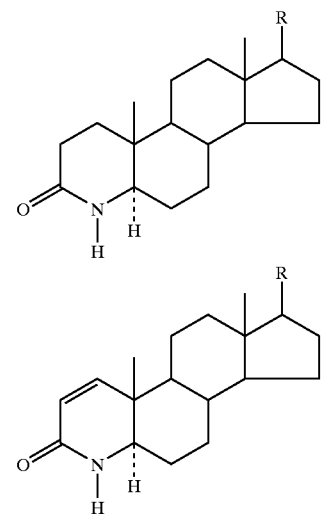

1a R=CONHC(CH₃)₃ 252–254° C.
1b=CONHC(CH₃)₂CH₂C(CH₃)₃ 224–226°

EXAMPLE 2

Methyl 4-Methyl-3-oxo-4-aza-5α-androst-1-ene-17β-carboxylate

A suspension of 25 g of the product of Example 1 and 2.25 g of sodium hydride in 500 ml of dry dimethylformamide was stirred under nitrogen for 15 minutes. Methyl iodide (15 ml) was added dropwise and the mixture was stirred for 30 minutes at room temperature. Additional (5 ml) methyl iodide was added and the mixture was heated at 50° C. for 2 hours. After cooling the mixture was diluted with water to a volume of 2 liters. The solid was separated after cooling and amounted to 25.4 g, m.p. 159–161° C.

In a similar fashion the following compounds were converted to their corresponding 4-methyl derivatives:

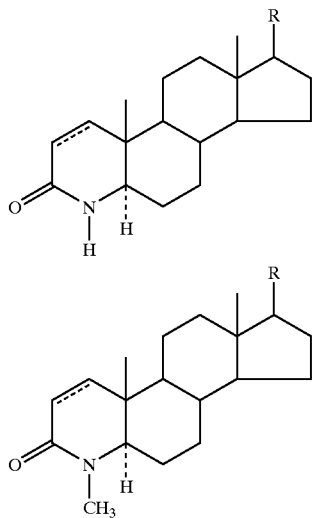

2a R=CONHC(CH$_3$)$_2$CH$_2$C(CH$_3$)$_3$, 148–150° C. androstane
2b=CONHC(CH3)3; Δ-1-androstene 153–155°
2c=CONHC(CH$_3$)$_2$CH$_2$C(CH$_3$)$_3$ 168–170° Δ-1-androstene

EXAMPLE 3

S-(2-Pyridyl) 4-Methyl-3-oxo-4-aza-5α-androst-1-ene-17β-thiocarboxylate

A suspension of 25 g of the product of Step 2 in 125 ml of methanol was treated with a solution of KOH (*12.5 g) in 12.5 ml of water. After refluxing for 4 hours, the solution was acidified with 6 NHCl and then was diluted with water. The crude acid (23.32 g) was separated, dried and had m.p. 300° C.

The crude, dry acid (23 g), triphenylphosphine (36.45 g) and 2,2'-dipyridyldisulfide (30.4 g) were suspended in 138 ml of toluene with stirring for 3 hours at room temperature. The reaction mixture was directly chromatographed on a column of 4.5 kg of silica gel eluting with 9:1 ethyl acetate-acetone to give 20.4 g of the desired product, m.p. 218–220° C.

Continued elution with acetone gave 5.2 g of the methanol addition product, S-(2-pyridyl) 1α-methoxy-4-methyl-3-oxo-4-aza-5α-androstane-17β-thiocarboxylate, m.p. 221–223° C. as a by-product.

3A. In a similar fashion the product of Example 1 was converted into S-(2-pyridyl) 3-oxo-4-aza-5α-androst-1-ene-17β-thiocarboxylate, m.p. 230–232° C.

3B. In a similar manner methyl 3-oxo-4-aza-5α-androstane 17-carboxylate was converted into S-(2-pyridyl) 3-oxo-4-aza-5α-androstane-17β-thiocarboxylate, m.p. 232–234° C.

EXAMPLE 4

N-t-Butyl 4-methyl-3-oxo-4-aza-5α-androst-1-ene-17β-carboxamide

Anhydrous t-butylamine was added to a suspension of 2.5 g of the pyridylthioester of Example 3 in 70 ml of tetrahydrofuran. After 60 minutes exposure, the resulting solution was evaporated and the residue was chromatographed on 125 g of silica gel. Elution with 20:1 ethyl acetate dichloromethane afforded 1.5 g of the product, m.p. 152–154° C.

When the example is repeated using an appropriate amine and an appropriate pyridylthioester, the following products were obtained:
- 4b: N-t-butyl 3-oxo-4-aza-5α-androstane-17β-carboxamide, m.p. 275–276° C.
- 4c: N-(2,4,4-trimethyl-2-pentyl) 4-methyl-3-oxo-4-aza-5α-androst-1-ene-17β-carboxamide, m.p. 168–170° C.

EXAMPLE 5

5-Oxo-3,5-Secoetian-3,20-dioic Acid

To a solution of 200 g of 3-oxo-4-etien-17β-oic acid in 3.5 l of t-butanol at 80° was added a solution of 198.4 g of sodium carbonate in 474 ml of water. A warm (65° C.) solution of 948.5 g of sodium metaperiodate and 6.95 g of permanganate in 3.5 l of water was added at such a rate that the reaction mixture was maintained at 80° C. After addition the mixture was heated at reflux for one hour. The mixture stood at room temperature overnight. The inorganic salts were removed by filtration and the cake was washed with 225 ml of water. A solution of 5% aqueous sodium bisulfite was added to reduce the iodine that was present. The t-butanol was removed under reduced pressure and the aqueous residue was acidified with conc. hydrochloric acid. The separated gum was extracted into dichloromethane and was washed with 5% aqueous sodium bisulfite, saturated sodium chloride solution, then dried and concentrated to an off-white residue (214 g). Crystalline material was obtained by suspending the residue in ether and diluting with hexane to give 152 g, m.p. 189–192° C.

EXAMPLE 5B

3-Oxo-4-aza-5-Etien-20-oic Acid

A suspension of 64.7 g of the dioic acid of Step 5 in 350 ml of ethylene glycol was treated with 80 ml of liquid ammonia. The resulting solution was heated at a rate of 3°/min. up to 180° C. and was held at that temperature for 15 minutes. After cooling, 1 liter of water was added and the mixture was acidified with 10% hydrochloric acid to a pH of 1.5. The product was removed and washed with water, then air dried to leave 57.5 g of the product, m.p. 310° C.

EXAMPLE 5C

3-Oxo-4-aza-5α-Etian-20-oic Acid

A solution of 136 g of the 5-acid of Example 5B in 16.32 ml of acetic acid was hydrogenated at 60° C. in the presence of platinum catalyst (from 16.32 g of PtO$_2$) at 40 psig for 3 hours. The catalyst was removed and the solution concentrated to give 128.2 g of crude product. The material was washed well with 3 l of water then filtered an air dried to leave 125 g of the white solid, m.p. 310°.

This material is also obtained by saponification of methyl 3-oxo-4-aza-5α-androstane-17β-carboxylate (methyl 3-oxo-4-aza-5α-etien-17β-oate) in 7% methanolic potassium hydroxide followed by an acidic work-up.

EXAMPLE 5D

N-(2,4,4-Trimethyl-2-pentyl)3-oxo-4-aza-5α-androstane-17β-carboxamide

A solution of 5.0 g of the product of Example 5C, 3.35 g of dicyclohexylcarbodiimide and 3.18 g of 1-hydroxybenztriazole in 500 ml of dichloromethane was stirred at room temperature overnight. The solid was separated by filtration and the filtrate was treated with 2,4,4-trimethyl-2-pentylamine (t-octylamine). This solution stood at room temperature for 64 hours. A small amount of solid was removed and the solution was washed successively with 10% aqueous sodium hydroxide, water, 10% hydrochloric acid and saturated aqueous sodium chloride. After drying and concentration the crude product was eluted through 240 g of silica gel with 3:7 acetone-dichloromethane to give 5.5 g of the product, m.p. 250–251° C.

EXAMPLE 5E

Example 5D is repeated using t-butylamine in place of 2,2,4-trimethyl-2-pentylamine to obtain N-t-butyl 3-oxo-4-aza-5α-androstane-17β-carboxamide, m.p. 274–276° C.

EXAMPLE 6

Synthesis of 17β(N-1-Adamantylcarbamoyl)-4-aza-5α-androst-1-en-3-one 100 mg of the 17-methyl ester (0.305 mmoles) from Example 1 was suspended in 3.0 ml of THF (dried over molecular sieves 3A), and then was added 183.0 mg of 1-adamantanamine (1.2 mmoles). The suspension was cooled to 5–10° C. and then 590 gl of 2.0 M solution, of EtMgBr in THF was added. The resulting mixture was allowed to stir for 10 minutes, and then refluxed for 1–2 hours under $N_2$. The mixture was cooled to 0° C. and then quenched with saturated solution of $NH_4Cl$ (about 10 ml.). The organic layer was separated and the aqueous layer extracted with three volumes $CH_2Cl_2$.

The organic layers were combined, washed 2 times with $H_2O$, twice with saturated sodium chloride, and dried over $MgSO_4$, filtered and evaporated to dryness in vacuum. Crystallization from EtOAc afforded 75.0 mg of product. Recrystallization from MeOH and drying at 110° C. for 2 hours/0.1 mm gave product, mpt. 305–306° C. Molecular weight (by FAB) showed $M^+$=451: Calculated=451.

Anal. Calcd. for $C_{29}H_{42}N_2O_2$: C, 77.28; H, 9.40; N, 6.21. Found: C, 76.84; H, 9.73; N, 5.93.

EXAMPLE 7

Synthesis of 17β(N-2-Adamantyl-carbamoyl)-4-aza-5α-androst-1-en-3-one

Following the above-described general procedure of Example 6 but utilizing 2-adamantamine (prepared by aqueous neutralization and EtOAc extraction and isolation) in place of 1-adamantamine, and refluxing for 7 hours in place of 1–2 hours, the title compound is prepared, mpt. 284–285° C.

EXAMPLE 8

Synthesis of 17β(N-1-Adamantylcarbamoyl)-4-aza-5α-androstane-3-one 100.0 mg of the adamantyl derivative produced in Example 7 was dissolved in 5.0 ml of dry THF. 300 mg of 5% Pd/C was added and hydrogenated for 6.0 hrs. at R.T. at 40 psi. The mixture was filtered through celite, the cake washed with THF (3 times) and solvent evaporated under vacuum to yield 97.0 mg. of crude above-titled product. NMR showed absence of olefins. The crude material was placed on 15.0 g silica gel column, and eluated with 1:1 ($CH_2Cl_2$: acetone).

Collected fractions afforded a single spot material by TLC weighing 77.98 mg. NMR was in excellent agreement with the proposed structure. Recrystallized from EtOAc to yield 65.59 mg of the above-titled product, mp. 323–324° C.

Anal. Calcd. for $C_{29}H_{44}O_2N_2$ 1/4 $H_2O$: C, 76.18; H, 9.81; N, 6.13. Found: C, 75.91; H, 9.97; N, 6.06.

EXAMPLE 9

Methyl 3-oxo-4-Methyl-4-aza-5α-androst-1-ene-17α-carboxylate

A suspension of 25 g of the titled product of Example 1 and 3.35 g of sodium hydride in 500 ml of dry dimethylformamide was stirred under nitrogen for 15 minutes. Methyl iodide (15 ml) was added dropwise and the mixture was stirred for 30 minutes at room temperature. Additional (5 ml) methyl iodide was added and the mixture was heated at 50° C. for 2 hours. After cooling the mixture was diluted with water to 2 liters. The solid was separated after cooling and amounted to 25.4 g of the above-titled product, m.p. 159–161° C.

EXAMPLE 10

S-(2-Pyridyl)-3-oxo-4-methyl-4-aza-5α-androst-1-ene-17β-thiocarboxylate

10(A) A suspension of 25 g of the product of Example 9 in 125 ml of methanol was treated with a solution of KOH (12.5 g) in 12.5 ml of water. After refluxing for 4 hours, the solution was acidified with 6N HCl and then was diluted with water. The crude acid (23.32 g) was separated, dried and had a m.p. 300° C.

10(B) The crude, dry acid of 10A, (23 g), triphenylphosphine (36.45 g) and 2,2'-dipyridyldisulfide (30.4 g) were suspended in 138 ml of toluene with stirring overnight at room temperature. Next day, crystallization set in. The reaction mixture was filtered, the residue washed with cold toluene, followed with cold anhydrous ether. Dried at 110° C. in vacuo to afford 20.4 g of the desired above-titled thiopyridyl ester m.pt. 218–220° C.

EXAMPLE 11

Synthesis of 17β(N-1-Adamantylcarbamoyl)-4-methyl-4-aza-5α-androst-1-en-3-one 120 mg of the thiopyridyl ester of Example 10 was suspended in 20 ml of dry THF, to the suspension was added 175.0 mg of 1-adamantanamine under $N_2$. The reaction was carried out at R.T. for 16 hours under $N_2$. The reaction was moni25red by silica gel TLC, using 1:1 acetone: hexane. After 6 hrs. the TLC showed that the reaction went exclusively to the product, with trace of starting material left behind. The product was separated on TLC 20 cm×20 cm, 1000 μm silica gel plate, eluted with 1:1 (acetone/hexane). The product was crystallized from ethyl acetate, to give 50.0 mg of pure material m. pt. 202–205° C. Molecular Weight (FAB) showed 465; Calc: 465. Recrystallization afforded 19.14 mg of the above-titled product, m.pt. 202–202.5° C.

Anal. Calcd for $C_{30}H_{44}N_2O_2.H_2O$: C, 74.64; H, 9.60; N, 5.80. Found: C, 74.32; H, 9.47; N, 5.89.

EXAMPLE 12

Hydrolysis of Methyl-3-oxo-4-aza-5α-androstane-17β-carboxylate

The 17β-androstane carboxylate starting material of Example 1 was hydrolyzed with 7% aqueous KOH in isopropanol or aqueous methanol, followed by an acidic work-up to give the corresponding 17β carboxylic acid which was utilized in Example 13.

EXAMPLE 13

N-(1-Adamantyl)-3-oxo-4-aza-5α-androstane-17β-carboxamide

A solution of 5.0 g of the product of Example 12, 3.35 g of dicyclohexylcarbodiimide and 3.18 g of 1-hydroxybenztriazole in 500 ml of dichloromethane was stirred at room temperature overnight. The solid was separated by filtration and the filtrate was treated with 1-adamantamine. This solution stood at room temperature for 64 hours, then filtered, and the solution was washed successively with 10% hydrochloric acid and saturated aqueous sodium chloride. After drying with $MgSO_4$, it was filtered and concentrated. The crude product was eluted through 240 g of silica gel with 3:7 (acetone-dichloromethane) to give 5.5 g of the above-titled product, m.p. 323–324° C.

EXAMPLE 14

Synthesis of Benztriazol-1-yl-3-oxo-4-methyl-4-aza-5α-androstan-17β-carboxylate

A suspension of 83.7 g of methyl-3-oxo-4-methyl-4-aza-5α-androstane-17β-carboxylate (See Rasmusson, et al. J. Med. Chem 29, 2298–2315, 1986) was hydrolyzed with 7% aqueous KOH in aqueous methanol, followed by an acidic work up to give the corresponding 17β-carboxylic acid.

The acid was readily converted into benzotriazyl-1-yl-3-oxo-4 methyl-4-aza-5α-androstane 17β carboxylate as described in Example 9. The activated ester (the benzotriazoyl derivative) was purified on TLC (4 plates, 20 cm×20 cm×20 cm×1000 μm silica gel) eluted with 4:96 (MeOH-$CHCl_3$). The isolated product was washed with ether to give the active ester m.pt. 198–200° C. with decomposition.

EXAMPLE 15

Synthesis of 17β(N-1 Adamantylcarbamoyl)-4-methyl-4-aza-5α-androstan-3-one 100.0 mg of the 4-methyl-4-aza-benzotriazole derivative prepared as described in Example 14, was dissolved in 20.0 ml $CH_2Cl_2$. To the clear solution was added 127 mg of 1-adamantamine. The reaction mixture was stirred overnight at $R.T./N_2$.

Crystallization from EtOAc after filtering the solution through Teflon Acrodisc CR afforded 26.32 mg, m.pt. 210–217° C. The product was further purified on 1.0 g silica gel column (EM silica gel) with 1:1 (acetone-hexane) as eluant to give after recrystallization 21.75 mg of white needles of the above-titled product, m.pt. 203–205° C.

Anal. Calcd. for $C_{30}H_{46}N_2O_2 \cdot 1.5 H_2O$: C, 73.58; H, 9.68; N, 5.62; Found: C, 73.15; H, 9.30; N, 5.67.

EXAMPLE 16

Diastereomeric Synthesis of 17β(N-exo-2-Norbornanylcarbamoyl)-4-aza-5α-androst-1-en-3-one)

100.0 mg of the correspondong 4-H thiopyridyl ester of Example 10 (See Rasmusson et al. J. Med. Chem. Vol. 29, pp. 2298–2315 (1986), was dissolved in 3.0 ml of dry THF under $N_2$. To the clear solution was added 477 μl of (±) racemic exo-2-aminonorbornane. Allowed the reaction to proceed for 16 hours at $R.T./N_2$. The reaction mixture was evaporated to dryness in vacuum.

The residue was dissolved in chloroform. The organic layer was washed with 2.5 N HCl acid (3 times); 3 times with water; 3 times with saturated NaCl solution, dried over $MgSO_4$, filtered and evaporated to dryness in vacuum to afford 56.3 mg of a diastereomeric mixture.

The crude product was chromatographed on TLC (2 plates, 20 cm×20 cm×500 μm silica gel) eluted with 70:30 ($CHCl_3$:acetone) to yield 43.4 mg. of the above-titled product. Recrystallization from EtOAc yielded 30 mg product, m.pt 245–245.9° C.

NMR ($CDCl_3$) confirmed the above structure. FAB mass spectrum calcd. for $C_{26}H_{38}O_2N_2$: m/e 411; Found: 411. Anal. Calcd. for $C_{26}H_{38}O_2N_2 \cdot H_2O$: C, 72.82; H, 9.40; N, 6.58. Found: C, 73.21; H, 9.20; N, 6.25.

EXAMPLE 17

Synthesis of 17β(N-1-Adamantylmethylcarbamoyl)-4-aza-5α-androst-1-en-3-one 200.0 mg of the thiopyridyl aza steroid, used in Example 16, was suspended in 2.0 ml of dry THF.

To the suspension was added 400 μl of 1-aminomethylene adamantane via syringe at $R.T./N_2$. After several minutes, a yellow clear solution resulted and after 1/2 hr., precipitation occurred. The reaction was allowed to proceed overnight/$N_2$. Diluted with $CH_2Cl_2$, washed with 10% NaOH, two times, then with $H_2O$ two times, followed by 10% HCl (two times), $H_2O$ (two times), and finally two times with satd. NaCl solution.

The organic layer was dried over $MgSO_4$, filtered, concentrated in vacuo to obtain the product, as shown by NMR, recrystallized from EtOAc, to yield 149.0 mg product, m.pt 255–257° C. with decomposition.

FAB Mass Spectrum, Calcd: m/e 464+1=465: Found 465.

What is claimed is:

1. A method of preventing prostatic carcinoma in human males who do not have benign prostatic hyperplasia and who are asymptomatic for prostatic cancer, which comprises of daily administering a therapeutically effective amount of a compound of the formula:

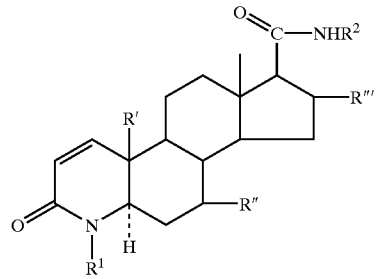

wherein:

$R^1$ is hydrogen, methyl or ethyl;

$R^2$ is monocyclic aryl containing 1 or more lower alkyl substituents of from 1–2 carbon atoms and 1 or more halogen (Cl, F or Br) substituents;

R' is hydrogen or methyl;

R" is hydrogen or β-methyl;

R'" is hydrogen, α-methyl or β-methyl.

2. A method according to claim 1 wherein the compound is systemically administered.

3. A method according to claim 2 wherein the compound is orally administered.

4. A method according to claim 3 wherein the compound is administered at a daily dosage of from 1 to 2,000 mg.

5. A method according to claim 4 wherein the compound is administered at a daily dosage of from 1 to 20 mg.

6. The method according to claim 5, wherein the compound is administered at a daily dosage of 5 mg.

7. The method according to claim 5, wherein the compound is administered at a daily dosage of 1 mg.

8. The method according to claim 1, wherein:

$R^1$ is hydrogen, or methyl; and

R', R", and R'" are each hydrogen.

* * * * *